United States Patent
Mäntele et al.

(10) Patent No.: US 7,812,312 B2
(45) Date of Patent: Oct. 12, 2010

(54) INFRARED MEASURING DEVICE, ESPECIALLY FOR THE SPECTROMETRY OF AQUEOUS SYSTEMS, PREFERABLY MULTIPLE COMPONENT SYSTEMS

(75) Inventors: Werner Mäntele, Blankenbach (DE); Oliver Klein, Frankfurt am Main (DE); Christian Zscherp, Freiberg-Ossenheim (DE); Andreas Barth, Sollentuna (SE); Hermann Von Lillienfeld-Toal, Gelnhausen (DE); Hellmuth Von Prollius, Berlin (DE); Frithjof von Germar, Mainz (DE); Heribert Offermanns, Hanau (DE)

(73) Assignee: Johann Wolfgang Goethe-Universitaet, Frankfurt am Main (DE)

( * ) Notice: Subject to any disclaimer, the term of this patent is extended or adjusted under 35 U.S.C. 154(b) by 793 days.

(21) Appl. No.: 10/510,017

(22) PCT Filed: Apr. 3, 2003

(86) PCT No.: PCT/EP03/03496
§ 371 (c)(1),
(2), (4) Date: Aug. 26, 2005

(87) PCT Pub. No.: WO03/083458
PCT Pub. Date: Oct. 9, 2003

(65) Prior Publication Data
US 2006/0043301 A1  Mar. 2, 2006

(30) Foreign Application Priority Data
Apr. 3, 2002  (DE) ............... 102 14 780
Apr. 3, 2002  (DE) ............... 102 14 781

(51) Int. Cl.
*G01J 5/02*  (2006.01)
(52) U.S. Cl. ............... 250/343; 250/339.1; 250/339.06; 702/28

(58) Field of Classification Search ............... 250/343, 250/338.1, 339.1, 339.06, 339.07, 339.08; 702/28
See application file for complete search history.

(56) References Cited

U.S. PATENT DOCUMENTS 3,803,384 A * 4/1974 Braunlich ............... 250/345
(Continued)

FOREIGN PATENT DOCUMENTS

DE  34 02 488  10/1984
(Continued)

OTHER PUBLICATIONS

MatWeb Online Material Data Sheet for Zinc Selenide. [online] Material Property Data, retrieved on May 18, 2007. Retrieved from the Internet: <URL: http://www.matweb.com/search/SpecificMaterialPrint.asp?bassnum=DSEN71>.*
(Continued)

*Primary Examiner*—David P Porta
*Assistant Examiner*—Mark R Gaworecki
(74) *Attorney, Agent, or Firm*—Marshall, Gerstein & Borun LLP

(57) ABSTRACT

The invention relates to an infrared measuring device, especially for the spectrometry of aqueous systems. Said device comprises at least one measuring unit, especially a measuring cell, also comprising at least one ATR-body and at least one infrared light source. The measuring unit contains at least one ATR-body which comprises at least two planar, substantially parallel limiting surfaces and which is transparent with respect to measuring radiation and which has an index of refraction which is greater than that of the medium which is arranged next to at least one limiting surface and which is to be examined, especially larger or equal to 1.5. The IR-measuring radiation on at least one of the planar, parallel limiting surfaces of the ATR-body can be totally reflected in an attenuated manner by at least six times.

47 Claims, 4 Drawing Sheets

U.S. PATENT DOCUMENTS

| | | | |
|---|---|---|---|
| 4,636,474 A | | 1/1987 | Ogura et al. |
| 5,214,286 A | | 5/1993 | Milosevic et al. |
| 5,278,413 A | | 1/1994 | Yamaguchi et al. |
| 5,434,411 A | | 7/1995 | Miyahara et al. |
| 5,436,454 A | * | 7/1995 | Bornstein et al. ...... 250/339.12 |
| 5,509,025 A | | 4/1996 | Capasso et al. |
| 5,772,606 A | * | 6/1998 | Ashibe et al. ............... 600/573 |
| 5,815,260 A | * | 9/1998 | Dou et al. .................... 356/301 |
| 5,905,030 A | * | 5/1999 | Okazaki et al. ............... 435/18 |
| 5,922,609 A | | 7/1999 | Kellner et al. |
| 6,484,044 B1 | | 11/2002 | Lilienfeld-Toal |
| 6,534,450 B1 | * | 3/2003 | Harrison et al. ............. 508/158 |
| 6,535,283 B1 | | 3/2003 | Heffels et al. |
| 6,584,335 B1 | | 6/2003 | Haar et al. |
| 7,110,112 B2 | * | 9/2006 | Uchida et al. ................ 356/364 |
| 2001/0025927 A1 | | 10/2001 | Ankerhold |
| 2002/0125589 A1 | * | 9/2002 | Katzir ........................ 264/1.23 |
| 2004/0024541 A1 | * | 2/2004 | Uchida et al. ................. 702/28 |
| 2004/0233433 A1 | | 11/2004 | Uchida et al. |
| 2004/0256563 A1 | | 12/2004 | Uchida et al. |

FOREIGN PATENT DOCUMENTS

| | | |
|---|---|---|
| DE | 3605518 | 8/1987 |
| DE | 42 00 869 | 7/1992 |
| DE | 43 24 141 | 3/1995 |
| DE | 43 33 560 | 4/1995 |
| DE | 197 48 849 | 5/1998 |
| DE | 197 34 618 | 2/1999 |
| DE | 198 56 591 | 6/2000 |
| DE | 100 15 615 | 10/2001 |
| EP | 0 206 433 | 12/1986 |
| EP | 0 670 492 A2 | 3/1995 |
| EP | 0 652 301 | 5/1995 |
| EP | 0 676 839 | 10/1995 |
| EP | 0 884 584 A1 | 12/1998 |
| JP | 05142142 A | 6/1993 |
| JP | 07239300 A | 9/1995 |
| JP | 07318564 A | 12/1995 |
| JP | 08015133 A | 1/1996 |
| JP | 08056565 A | 3/1996 |
| JP | 08201279 A | 8/1996 |
| JP | 08278199 A | 10/1996 |
| JP | 08327533 A | 12/1996 |
| JP | 09061345 A | 3/1997 |
| JP | 09311099 A | 12/1997 |
| JP | 09 281102 A | 1/1998 |
| JP | 10 090271 A | 7/1998 |
| JP | 2001025465 A | 1/2001 |
| JP | 2001249073 A | 9/2001 |
| WO | WO-96/10198 | 4/1996 |
| WO | WO-97/32198 A1 | 9/1997 |
| WO | WO-99/05509 | 2/1999 |
| WO | WO-99/66312 | 12/1999 |
| WO | WO-03/074993 A1 | 9/2003 |
| WO | WO-03/078981 A1 | 9/2003 |

OTHER PUBLICATIONS

Hesse et al., "Spektroskopische Methoden in der organischen Chemie," Chapter 2, pp. 39-92 (1984).

Lubos et al., "Quantum Cascade Lasers for Mid-Infrared Spectroscopy," *Vibrational Spectroscopy*, Sep. 18, 2002.

Notice of Reasons for Rejection from Japanese Application No. 2003-580846.

* cited by examiner

INFRARED MEASURING DEVICE, ESPECIALLY FOR THE SPECTROMETRY OF AQUEOUS SYSTEMS, PREFERABLY MULTIPLE COMPONENT SYSTEMS

This is the U.S. national phase of International Application No. PCT/EP03/03496 filed Apr. 3, 2003, the entire disclosure of which is incorporated herein by reference.

The present invention concerns infrared measuring devices, especially for aqueous systems, which comprise at least one measuring unit, especially a measuring cell, containing at least one ATR body as well as at least one infrared light source. Furthermore, the invention concerns the use of the infrared measuring device according to the invention for the qualitative and quantitative determination of components, especially essentially simultaneously, especially in aqueous systems, preferably in multicomponent systems.

Infrared spectroscopy is sufficiently well known to the person skilled in the art and is used especially in organic chemistry for the determination of functional groups (see Spektroskopische Methoden in der organischen Chemie [Spectroscopic Methods in Organic Chemistry], M. Hesse et al., Georg Thieme Verlag, Stuttgart, 1984, Chapter 2), whereby samples can be measured in all three states of aggregation, as well as in the dissolved state. In addition to use in structural clarification, it has already been proposed to use IR spectroscopic methods in process analysis.

In DE 36 05 518 A1, a measuring cell is described for IR spectroscopy in which absorption and emission spectra can be recorded continuously, even on small amounts of sample, so that, for example, sample fractions separated by chromatography can be detected continuously. A measuring cell is used which has so-called ATR crystals (ATR=Attenuated Total Reflection). The infrared light source used is one with a continuous spectrum. As long as the surface of the ATR crystal, forming an inner wall of the measuring cell, is to be provided with a stationary phase of a chromatography method, in order to investigate a sample flowing through the measuring cell, it has been proposed to carry out measurements by ATR fluorescence, phosphorescence or Raman spectra parallel to the above or subsequently. In order to be able to measure very small amounts of sample, a measuring cell is disclosed in DE 36 05 518 A1, the middle region of which is filled by an additional element, as a result of which the construction of this measuring cell becomes very complicated and plugging during flow can no longer be excluded. Then, in order to still be able to carry out the measurement, mostly the entire measuring cell has to be replaced. Otherwise, no information can be derived from DE 36 05 518 about the continuous control of chromatographic methods, regarding if or optionally certain substances can be determined qualitatively or quantitatively with the described measuring cell.

DE 100 15 615 A1 describes a measuring arrangement for the detection of traces of gaseous substances which are present in extremely low concentrations. Here, we are dealing with a gas measuring system with an open optical measuring section for spectroscopic measurement of at least one component of a gaseous sample with a laser source, containing a reference gas sample for the gas to be measured, two radiation detectors for the main beam and reference beam, and at least two radiation reflectors. With the gas measurement system disclosed, for example, optical measuring sections of 1 to 200 meters can be measured, and a retroreflector can be eliminated. Quantum cascade lasers emitting a pulsed radiation in the near to middle infrared region or a laser diode emitting continuous radiation in continuous operation in the near infrared region, which emits a very divergent beam bundle with an opening angle $\alpha$ of approximately 35° are used as laser sources. With the gas measurement system according to DE 100 15 615 A1, gases, such as hydrogen sulfide, ammonia, hydrochloric acid and methane can be detected.

According to DE 43 24 141 A1, low isopropanol contents (<10%) can be determined continuously in damping agents for printers when operating with a pulsed IR radiation source according to a modified four-beam method. Again, the infrared source under consideration is one with a continuous spectrum in the near infrared region. Other data regarding the infrared measurement method cannot be derived from this document either.

In order to be able to determine the concentration of components in aqueous liquids reliably and reproducibly, according to DE 197 48 849 A1, the analyte to be measured is to be subjected to a chemical reaction before the measurement, which leads the other components of the liquid sample unchanged. Moreover, the chemical reaction with the analyte has to be such that satisfactory IR spectrometric concentration determination is made possible. Again, the infrared sources used are not different from the conventional infrared sources having a continuous spectrum. This procedure for the determination of polar substances in aqueous systems is also very cumbersome and cost-intensive and, moreover, is limited to only a few analytes, that is, those which undergo the required chemical reaction.

In the production of alcoholic and nonalcoholic beverages, it is necessary to be able to determine the concentration of particular components at any arbitrary point in time, if possible, suitably in a continuous manner, in order to minimize product rejection and in order to be able to ensure as high quality as possible. For example, the content of sugar or alcohol in beverages is still determined with density measurements in spite of the spectrometric methods which have been developed further and have become available in the meantime. The density measurement method is very expensive, requires refined and demanding measurement technology and is suitable only to a limited extent for continuous measurements, that is, for example, for on-line use.

Especially, in the case of high quality wines, at the present time the question of genuineness of the selected product has to be determined reliably and mostly this can only be done with the aid of very costly techniques, such as multidimensional NMR spectroscopy. In addition, such NMR equipment has to be operated with highly qualified technical people and they are also needed to evaluate the spectra obtained in this way.

Moreover, for example in medical diagnostics, even for routine investigations of blood or urine, usually large amounts of samples are necessary, which brings about high material expenditure as well as personnel expenditure and is frequently considered to be unpleasant by the treated patients as well as by the personnel.

DE 197 34 618 A1 describes an analytical device for in-vivo analysis in the body of a patient. Here, we are dealing with an infrared measuring device in the form of a cannula that can be inserted in the skin and which is designed for the spectrometry of interstitial fluid in the skin tissue, especially for the detection of glucose, and uses an ATR body as well as at least one quantum cascade laser. The measurement is carried out with the aid of an optical fiber, into which the radiation is coupled, and which is perforated, at least over a partial section, so that interstitial fluid can arrive through the wall of the cannula to a measurement section of the optical fiber placed in the cannula. In order to eliminate perturbation caused by larger molecules, such as proteins, and to achieve sufficient measurement accuracy, according to DE 197 34 618 A1, the optical fiber is to be covered with a semipermeable membrane. Furthermore, using suitable sealing measures, it is ensured that the interstitial fluid cannot arrive at the optical fiber to a perturbing extent through the remaining gaps. In order to ensure this, additional epoxy resins are to be applied. In order to protect the optical fiber against corrosion, it can be provided with a very thin evaporated metal layer consisting, for example, of silver. The usually very thin optical fibers can be perforated frequently only with expensive laser boring methods with a pore content of preferably at least 50%, the manufacture of the cannulas according to DE 197 34 618 A1 is therefore very time-consuming and cost-intensive.

WO 96/10198 describes a special embodiment for an optical fiber suitable for ATR spectroscopy. This optical fiber has a core which is transparent to the radiation and a covering layer surrounding the core, the covering layer reflecting this radiation on its inner wall. Along a partial section, an essentially hemicylindrical element was removed from the optical fiber so that it has a single plane surface where the radiation that is coupled in can undergo total reflection. Care is taken that the cover has a thickness over the entire length of the optical fiber which does not allow the evanescent field of the coupled-in radiation to enter into interaction with a medium surrounding the optical fiber, since targeted interaction should take place only on the plane surface of the described partial section. Other data cannot be derived from this document.

EP 0 206 433 A2 discloses an immersion probe for IR spectroscopy, containing a prism, into which measuring radiation can be coupled through optical fibers. The prism used for the measurement has at least two measuring surfaces arranged next to each other at an angle. In order to achieve sufficient measurement accuracy, the method of EP 0 206 433 A2 requires, for the concentration determination of substances, reference measurements with at least two calibration media in which the substance to be investigated is present at a known concentration.

DE 198 56 951 A1 also describes an ATR probe which has a cylindrical protective housing at the free front end of which a prism is arranged, which has a surface that can be wetted with the medium to be analyzed and on which a coupled-in light beam is reflected. According to DE 198 56 951 A1, the fluid media can be analyzed spectroscopically with such a probe by using two separate light beams, the angles of incidence of which onto the wettable surface of the prism differ and/or their state of polarizations differ. For example, the refractive index n and the absorption coefficient k can be calculated numerically from the wavelength-dependent reflection coefficients and this can be done for both angles.

DE 42 00 869 A1 discloses an infrared microscope spectrometer with which spectrometric ATR measurement can also be performed and in which the optical axis can be adjusted easily.

According to Hvozdara et al. (Summary of the Conference Report of the International Conference on Advanced Vibrational Spectroscopy ICAVS, Turku, Finland, August 2001), using radiation in the middle infrared region, sensors employing the principle of attenuated total reflection can be employed, utilizing the absorption of evanescent waves for the analysis of aqueous media. For example, in this way, an analyte, enriched in a suitable polymer coating, can be investigated. Although it is indicated that new applications should open by the utilization of quantum cascade lasers, no further details are given regarding this wishful statement.

EP 0 670 492 A2 is concerned with the determination of substances contained in urine, using detection and analysis of the absorption behavior of radiation in the visible and in the near-infrared region with the aid of the multivariant regression analysis. Here, suitable wavelengths are selected considering a certain correlation coefficient between the concentration and the absorption ability of an aqueous solution, including correspondingly standardized aqueous solutions of the analyte to be investigated.

In DE 43 33 560 A1, a measuring cell containing an ATR crystal in the form of an immersion probe is described, which can be used for on-line control of chemical production processes, even under high pressure and at high temperature, and requires only small maintenance expenditure. This is achieved by the fact that an ultrasound source for cleaning the measuring surface from product residues is arranged in front of the measuring surface of the ATR crystal. The ATR measuring cell according to DE 43 33 560 A1 is designed as an incorporated probe for a chemical reaction and has a measuring surface facing the production chamber, as well as a metal-coated back side. For the purpose of evaluation of the measuring radiation, the measuring beam leaving the ATR crystal is introduced through a fiber-optic waveguide cable into an FT-IR spectrometer. Further data regarding the limitations and possibilities as well as applications which go beyond the use in chemical process technology cannot be derived from this document.

In U.S. Pat. No. 5,214,286, a device is described that can be used in IR spectroscopy, with which it should be possible to adjust the round cross-sectional shape and the size of the radiation used in the FT-IR spectrometer to IR elements which still originate from dispersively operating spectrometers.

According to WO 99/05509, an ATR body is used to analyze biological molecules, which are preferably applied in the form of a so-called monolayer onto at least one side of the ATR body onto which a very thin metal layer had been applied. Preferably, gold layers with a thickness of 5 to 10 nm are used. The measuring radiation corresponding to the ATR body is preferably evaluated using an FT-IR spectrometer.

Solids can also be analyzed according to WO 99/66312 directly with the aid of an IR spectrometer based on the use of an ATR body. Here, the solid sample is pressed at high pressure onto the surface of the ATR crystal. For such an application, ATR prisms based on diamond materials have been found useful. In order not to falsify the measured result by attenuated total reflecting interaction with the pressing device, a reflective layer is incorporated between the prism that couples the measuring radiation in and out over a large area of the ATR body facing the measuring medium; this layer transmits only the radiation that is coupled in and out. The measurement of liquid or other systems with the aid of the described IR spectrometer device is not discussed anywhere in WO 99/66312.

In EP 0 652 301 A1, a plasma coating method is described for the preparation of a thin, diamond-like carbon coating with the aid of a pyrolytic graphite cathode. In any case, in this document, there is no indication at all that, under the described conditions of plasma coating, high quality coated ATR bodies are also accessible.

Therefore, it would be desirable to be able to have devices and methods with which even small and even very small amounts of components, especially in aqueous systems, could be determined qualitatively and quantitatively in a simple manner and very rapidly and accurately.

Therefore, the task of the present invention was to find a measuring device which is simple to produce and handle and which, moreover, is characterized by extreme robustness, even in continuous operation, for example, under production conditions in the manufacture of beverages, as well as by extreme precision in the qualitative as well as quantitative determination of components in liquids. Furthermore, the task of the invention was to be able to analyze simultaneously or almost simultaneously several components or contents which are present together in an aqueous liquid.

Accordingly, an infrared measuring device was found in which the measuring unit contains at least one ATR body, which has at least two plane, essentially parallel boundary surfaces, which is transparent to the measuring radiation and which has a refractive index which is higher than that of a medium to be investigated, which is adjacent to at least one boundary surface, especially higher than or equal to 1.5, where the IR measuring radiation can undergo attenuated total reflection least six times on at least one of the plane, parallel boundary surfaces of the ATR body. The plane boundary surface of the ATR body accordingly advantageously has a continuous uniform measuring section within which a measuring beam can undergo attenuated total reflection at least six times, that is, it can interact with an adjacent medium.

Even more preferably, the plane, essentially parallel boundary surfaces, are essentially not metal coated or are completely not metal-coated, thus do not have a metal-coated surface or are not adjacent to one such surface.

Quantum cascade lasers, which are suitable for the measuring device according to the invention are known, for example, from EP 0 676 839 A as well as from U.S. Pat. No. 5,509,025, in which their fundamental mode of operation as well as their structure are described. Preferably, quantum cascade layers are used, which radiate electromagnetic radiation in the middle infrared region. For the infrared measuring device according to the invention, for example, those quantum cascade lasers come into consideration which emit only a defined frequency, especially in the middle infrared region, as well as also those which emit two, three, four, five or more frequencies, especially in the middle infrared region. Furthermore, those quantum cascade lasers are also used which emit defined frequency bands. Naturally, these infrared measuring devices can also be equipped not only with one, but also with two or more of the quantum cascade lasers described above. When, in a measuring device according to the invention, a quantum cascade laser is used which is able to emit electromagnetic radiation in at least two different frequencies, especially from the middle infrared region, or if several quantum cascade lasers are used together in such a measuring device, the electromagnetic radiation, especially when it has different frequencies, can be emitted at the same time or almost at the same time or in a sequence in time. In this way, it is possible to characterize the spectrometric behavior of a substance in a sample comprehensively. Furthermore, it is possible to investigate several components present in the sample in a very short time, that is, simultaneously or almost simultaneously. Almost simultaneously or simultaneously, in the sense of the present invention, means that the signals are emitted so little separated in time that, in the detected absorption signals, no significant differences can be detected from absorption signals obtained when the radiation was sent absolutely at the same time.

In a preferred embodiment, the quantum cascade laser used emits electromagnetic radiation in the form of pulses with defined duration and/or intensity. This pulse duration and/or intensity can be freely selected in a wide range and can be used to produce spectrometric investigation conditions optimized for each component to be investigated. Thus, when several components are to be measured in a sample, depending on the frequency of the emitted electromagnetic radiation, pulse durations of different lengths and/or different intensities can be selected. For example, components with weakly absorbing chromophores can be exposed to pulses with a longer pulse duration, while in the case of strongly absorbing substances, very short pulse durations are sufficient for being able to detect a satisfactory signal. Even this different absorption behavior can be utilized in the analysis and in an evaluation unit in working relationship with a detector, these can be stored for immediate evaluation or they can be incorporated in a suitable analysis program. Accordingly, with the infrared measuring device according to the invention, it is possible to emit electromagnetic radiation of different frequencies, either from only one quantum cascade laser, but also by the use of several quantum cascade lasers, in an arbitrary sequence, for example, sequentially. This applies also especially to the pulsed radiation described above.

Through the free selection of the pulse sequence of the radiated frequencies of the electromagnetic radiation, according to the invention, pulse patterns and/or intensity patterns can be used which are designed for the particular analytical problem. For example, if the components present in a fluid or possibly present in a fluid are known or suspected to be present with reason, the pulse durations and/or intensities can be predetermined, so that, through the nature and intensity of the detected signals, one can determine directly as to which components are present in what concentrations in the investigated sample, with the aid of an evaluation unit, especially a computer-supported evaluation unit. These patterns of pulse sequence, pulse length and/or pulse intensity at two or more frequencies, can be used again to produce certain patterns in the response signals, which are characteristic for certain compositions. In this way, it is possible to determine within a very short time if and in what concentration certain components are present in a sample. Especially preferably, accordingly, electromagnetic radiation of different frequency and/or intensity can be emitted according to a multiplex pattern, especially in the pulsed manner. Thus, known multiplex spectrometers or electric multiplexers, which are used mainly on the detector side, can be employed. On the other hand, preferably, according to the invention, those multiplexers can also be used which influence not only the detector or exhibit a wavelength-specific control but also select the wavelengths and/or intensities to be emitted and control the radiation sequence or radiation pattern. The multiplexer to be used according to the invention controls or regulates in addition also the intensity of the particular measuring radiation, even other embodiments, especially depending on the particular measurement problem. These so-called optical multiplexers thus coordinate the radiation source and detector and adjust these to one another. Among others, such multiplexer switch a pulse sequence adjusted to the particular measurement program on and off, especially with wavelength-dependent modulation of the intensity and consequently control the light source. Preferably, the detected signals are evaluated with the aid of known methods, such as factorial analysis, multiple least square algorithms or with neuronal network analysis. Commonly, computer-supported evaluation units are used for this.

Moreover, using quantum cascade lasers, it is possible to send not only radiation at different frequencies and/or intensities in a given time sequence to the ATR body. Rather, one can also radiate different frequencies simultaneously, where especially the number and frequency of the emitted radiations can be varied continuously. In this way, frequency patterns can be composed which generate characteristic absorption signals for the compositions to be investigated, as a result of which multicomponent mixtures, especially those in aqueous systems, can be analyzed in a short time. The analytical method described above can also be designated as matrix coding/matrix decoding.

The embodiment of an FT-IR measuring device according to the invention has at least one light source, which is able to emit a continuous or a multiwavelength spectrum continuously. Such light sources are known to the person skilled in the art, for example, as Nernst pins, which are made essentially of zirconium oxide with rare earth additives, as well as the so-called globars, consisting essentially of silicon carbide. Furthermore, electrically conducting ceramics come into consideration as light source. Fundamentally, light sources can be used which emit over the entire spectral infrared region or only through certain regions of this spectrum. In order to determine components with the FT-IR measuring device according to the invention, preferably those light sources come into consideration which emit electromagnetic radiation in the middle infrared region, that is, in the region from about 2 μm to about 25 μm, especially from about 2.5 μm to about 12 μm.

The interferogram recorded in the detector of the FT-IR spectrometer device, in which the superimposition of all wavelengths occurring in the spectrum is recorded, is decomposed in the evaluation unit by computer-aided Fourier transformation into the frequencies of the individual vibrations. For details on Fourier transformation, see, for example, N. B. Colthup, L. H. Daly, S. E. Wiberley, Introduction to Infrared and Raman Spectroscopy, Academic Press, San Diego, 1990, to which reference is made herewith. With the FT-IR measuring device according to the invention, several components can be determined essentially simultaneously with high sensitivity, at high speed and with precise wavelength identification.

The current systems used in infrared measuring devices can be employed as detectors for the recording of the measuring radiation.

In case the detected signals should be processed or evaluated further, evaluation units commonly known to the person skilled in the art can be employed, especially computer-aided evaluation units. An evaluation unit in the sense of the present invention can also include data storage units and/or a display unit, for example, a printer or a screen. Naturally, these elements can also be present separately.

In a preferred embodiment, the measuring device according to the invention has a replaceable evaluation unit. For example, a first evaluation unit can be replaced by a second or other evaluation unit. This can be done after the completion of a first measurement, after a completed measurement and also during a measuring process, for example, if it is determined that a compound searched for is not present or could be simply detected, so that it can be used in the search for another component. The advantage of this is that, for example, in a first evaluation unit, an evaluation program is present for a given analytical problem, which can be replaced by a second or other evaluation unit when the task is changed, which other unit has an evaluation program designed for the new problem to be solved. Preferably, the evaluation units are present in the form of evaluation modules with which working relationships with the measuring device according to the invention, especially with the detector, can be established in a simple manner, for example, using plug-in or insertable modules. It was found to be advantageous to make the evaluation units distinguishable by giving them a different shape and/or color. Furthermore, two or more evaluation programs can be present in an evaluation unit, which can be freely switched to a particular mode of execution, depending on the need.

For example, through the evaluation unit, the multiplexer can also be influenced or controlled. Thus, with the evaluation unit, the radiation source(s) or the choice of frequency, pulse sequence and intensity assignment of the radiated measuring radiation can be influenced with the evaluation unit for a given analytical problem.

The measuring unit used in the infrared measuring device according to the invention contains at least one ATR body. ATR bodies are also called ATR crystals in the state of the art, although these systems do not necessarily have to be in the crystalline form. Accordingly, for example, a sintered silver chloride can also be a properly functioning ATR body/crystal. Fundamentally, in this connection, those ATR bodies are suitable which are entirely or partly transparent to the measuring radiation.

As the material used for the ATR body, any arbitrary material comes into consideration, which is transparent to the radiation used, especially to electromagnetic radiation in the middle infrared region and, moreover, has a high refractive index and has a refractive index which is higher than that of air and/or of a medium to be analyzed with the infrared measuring device according to the invention. Suitable materials for the ATR body include diamond, sapphire, cadmium telluride, thallium bromide/iodide, silicon, germanium, zinc selenide, zinc sulfide, magnesium difluoride, cesium iodide, silver chloride, calcium difluoride, potassium bromide or sodium chloride. It is obvious to the person skilled in the art that some of the above materials cannot come into consideration for measurement in aqueous systems because of their solubility in water, for example, an ATR body made of sodium chloride. In another embodiment, ATR bodies with a material that is transparent to infrared radiation are used, especially a polymeric material with a refractive index, preferably $\geq 1.5$, especially one made of polyethylene.

The ATR body preferably forms a side wall of the measuring unit or measuring cell with at least one plane boundary surface. Provided that the ATR body has two plane essentially parallel boundary surfaces, this ATR body can also have any arbitrary geometry as long as this permits the adjustment of an impinging beam in such a way that, before leaving the ATR body, it will have undergone attenuated total reflection at least twice or three times, preferably at least six times, preferably at least seven times on one or several plane, essentially parallel boundary surfaces. In an embodiment of the invention with six or seven such total reflections, already optimum analytical results are achieved regarding sensitivity, accuracy and speed, even in the case of aqueous multicomponent systems. In this case, the ATR body must have such a shape and size that the at least six or seven attenuated total reflections occur along a measuring section. Measuring section is defined here as that section of the ATR body which enters into contact with the medium to be analyzed and which is available on the whole for attenuated total reflections.

In another embodiment, at least two boundary surfaces of the measuring unit or measuring cell, especially opposite walls of the measuring cell each consist of an ATR body, especially each consists of an ATR body having at least two plane, essentially parallel boundary surfaces. Moreover, the entire measuring cell can be made of an ATR body.

In a further, preferred embodiment, the measuring cell is a flow-through cell. This has the advantage that, for example, processes in different manufacturing methods, for example, preferably in the on-line mode, can be investigated. These flow-through cells are especially suitable for use in process analysis and in the investigation of body fluids, for example, blood.

Moreover, it is also possible to make the measuring cell or the ATR body as an immersion probe, for example, in order to analyze with the aid of the infrared measuring device according to the invention sample systems which otherwise can be measured only poorly or not at all.

Such an immersion probe is especially suitable also as random sample controls in a wide variety of methods, in which an aqueous as well as nonaqueous systems are being used. For example, when using an immersion probe, urine, blood, fruit juices, beer, spirits, wine, washing liquors or waste water can be investigated for components in a simple way, for example, for polar substances, such as saccharides, for example, glucose, alcohols, for example, ethanol, or phosphoric acid esters. Furthermore, analysis of components in milk and dairy products, such as quarg or yogurt is also possible without these products having to be specially prepared.

In another embodiment, at least one boundary surface of the ATR body which is exposed or can be exposed to the medium to be analyzed, is provided with a coating, which is transparent to the measuring radiation. Especially when the coating has a thickness which is lower than the wavelength of the measuring radiation used, any coating material which is transparent to the measuring radiation can be used. On the other hand, the thickness of the coating is not critical when the coating material is one for an ATR body, that is, which has a refractive index which always approximately corresponds to that of the ATR body used. For example, an ATR material, such as zinc sulfide or zinc selenide, which is especially preferably used for the ATR body according to the invention, can be provided with a layer made of diamond. In this way, an ATR body is obtained which has an extremely resistant and inert coating. Especially preferably, the diamond layer is applied according to a method described by H. J. Neubert in Optics, February 2002, page 11. According to this, a temperature in the region from 15,000 to 20,000° C. is produced in the neighborhood of a surface with the aid of a carbon dioxide laser with a power of about 6 to 7 kW. A plasma is produced by introducing argon into this region. When a gaseous hydrocarbon, for example, methane, is introduced into this plasma, free carbon atoms are formed which can be deposited on a substrate, in the present case onto a plane boundary surface of an ATR body, forming a diamond layer of very low thickness. For example, the coating described above is especially advantageous for materials for ATR bodies which are toxic, soluble, for example, in the sample medium, and/or are sensitive to mechanical stress. ATR bodies made of zinc sulfide or zinc selenide, which are provided with a coating, especially a diamond coating, are especially suitable for the measuring device according to the invention.

In a preferred embodiment, the coating of the ATR body of the infrared measuring device according to the invention has a thickness which is smaller than preferably half of the wavelength of the infrared measuring radiation used, especially those having a thickness in the range from 2 nm to about 25 µm, especially preferably, from about 2 µm to about 12 µm, as well as especially about 5 µm. A suitable coating thickness range extends from 2 nm to 12 µm. The thickness of the coating especially preferably lies in a region of about one-fourth of the measuring wavelength. Furthermore, it is recommended to use a coating which is homogeneous with regard to thickness and composition and has as smooth a surface as possible. Here, it is advantageous when the unevennesses in the coating do not exceed the value of about one-fourth of the measuring wavelength on the average. Suitably, those coatings are used which do not reflect the measuring radiation, not even partially. The coating fulfills a double function, by first of all protecting the medium being measured from contamination with any toxic ATR body material, and, on the other hand, protecting the ATR body against mechanical damage. In the investigation of aqueous systems, especially those coatings were proven to be useful which do not allow diffusion of water molecules through this layer to the ATR body.

In another preferred embodiment, instead of a diamond coating, a layer made of a transparent or translucent plastic, especially polyethylene, can also be used.

In another advantageous embodiment, the AT body materials that can be coated are selected from sapphire, cadmium telluride, thallium bromide/iodide, silicon, germanium, zinc sulfide, zinc selenide, magnesium difluoride, cesium iodide, silver chloride, calcium difluoride, potassium bromide and sodium chloride, with zinc selenide and zinc sulfide being preferred.

Especially, also by the fact that, in the infrared measuring devices according to the invention, electromagnetic radiation of two or more frequencies can be used simultaneously, when using a measuring cell as well as especially when using an immersion probe, the system to be investigated is contacted only briefly and generally with no destruction.

In an advantageous embodiment of the invention, the measuring unit represents a pressure-resistant measuring unit. A measuring unit according to the invention, especially measuring cell, is characterized accordingly also by the fact that the measuring unit contains at least one ATR body which comprises at least two plane, essentially parallel boundary surfaces, is transparent to the measuring radiation and has a refractive index which is higher than that of the medium to be investigated adjacent to at least one boundary surface, preferably it is higher than or equal to 1.5, where the measuring unit is pressure resistant. Pressure resistant in the sense of the present invention should be understood to mean that the measuring unit functions essentially satisfactorily even at high external pressures as well as at high internal pressures, so that, for example, no leaks or damage occur and that the measuring process is not disturbed by the high external pressure. Preferable the measuring cells used are especially flow-through cells, such as immersion probes, pressure resistant, especially at external pressures up to about 100 bar. Those measuring units were found to be especially expedient which are stable in the range from 1 to 25 bar. Especially also the ATR bodies should be designed so that they are resistant to pressure and, for example, have the appropriate thicknesses. Pressure-resistant measuring units are suitable, for example, for use in process analysis, for example, without having to change the manufacturing conditions, they can follow the actual progress of the manufacturing process in real time. Pressure-resistant measuring units can consequently be used in beverage manufacture, for example, during the manufacture of beer, but also in chemical processes. Hereby, it is also of advantage that, with the measuring device according to the invention, using a pressure-resistant measuring unit, polar substances, for example, carbohydrates and alcohols can be determined qualitatively and quantitatively.

With the infrared measuring device according to the invention, both individual components but also complex mixtures of components can be investigated and characterized in sample systems unequivocally and exactly, especially using electromagnetic radiation in the middle infrared region, whereby the components can be determined especially in aqueous systems qualitatively and/or quantitatively.

Thus, for the first time, an infrared measuring device is available which can also be used in on-line operation and which is suitable for the analysis of aqueous systems, such as especially beer, wine, spirits, soft drinks, fruit juices, waste water, washing liquors, process fluids or body fluids, such as blood, saliva, lymph or urine. For example, it is possible to determine the sugar and/or alcohol content, for example, the glucose and/or ethanol content in liquids simultaneously or almost simultaneously. If the components that are possibly present in a sample are known, the search for the signals to be detected can be limited to quite specific frequencies or frequency regions, as a result of which very high sensitivities can be achieved. For example, with the aid of the infrared measuring device according to the invention, different saccharide compounds present together in aqueous systems can be identified, for example, fructose, glucose and galactose.

In a preferred embodiment of the invention, for example, components of beverages, such as beer, wine, spirits, milk, dairy products, soft drinks or fruit juices, can be determined qualitatively and quantitatively during manufacture or processing and/or during filling with the aid of the FT-IR measuring device according to the invention using a flow-through cell. These components, which optionally also occur together, can be, for example, alcohols, such as ethanol, methanol, propanol or butanol, carbohydrates, carbon dioxide and/or proteins, whereby the components can be analyzed together, independently of their size.

In an embodiment according to the invention, the device according to the invention is used to determine the components of fruits and vegetables quantitatively and/or qualitatively. Here, in an embodiment, a plane surface of an ATR body of a measuring unit can be placed or pressed, for example, onto freshly cut pulp of fruits or vegetables. A hollow body, which will be described below, which is equipped with an ATR body, is especially well-suited for these measurements. Similarly, for example, the degree of ripeness of grapes can be determined by immersing an ATR body, for example, in the form of an immersion probe or the above-mentioned hollow body, which is in working relationship with an infrared measuring device according to the invention, is placed into direct contact with the fruit pulp or is immersed into it.

The infrared measuring device according to the invention is especially suited for the determination of components, especially in medicine or veterinary medicine. For example, components can be detected qualitatively and/or quantitatively in body fluids, such as blood, urine, saliva or lymph. In this way, prerequisites for a rapid diagnosis are created. Thus, for example, with the aid of a flow-through cell and if desired even on-line, that is, in real time mode, components in the blood, such as glucose, ureas, creatinine or triglycerides, as well as alcohols, for example ethanol, can be determined. The infrared measuring device according to the invention can also be used, for example, in dialysis. The replaced blood can be tested continuously for especially relevant or critical components and the time in which the blood is sufficiently purified can be determined exactly. As a result of this, unnecessarily long dialysis times can be eliminated. Also, due to the fact that the ATR body can have small dimensions, it is no problem to use replaceable or recyclable flow-through cells in dialysis. Expediently, such a flow-through cell is designed as a module, so that it can be integrated into a measuring section, for example, in a blood-conducting cannula.

Information about the status of the blood to be purified during dialysis can also be provided with the aid of spectroscopic investigation of the washing- or exchange fluid during the purification of the blood with the aid of the infrared measuring device according to the invention. According to the invention, the said measuring device is also used for the determination of components in this washing fluid. This involves the advantage that the measurement no longer has to take place under sterile conditions and still rapid conclusions can be made about the state of the purified blood.

However, for the determination, for example, the above blood components with the device according to the invention, even amounts of just 100 µL are sufficient, especially when the measuring device according to the invention has a radiation source that emits a continuous spectrum; even amounts <20 µL can be analyzed, especially when the measuring device according to the invention uses a quantum cascade laser and these amounts are sufficient to obtain exact data on the substances that are present, for example, in blood and on the concentrations at which they are present. In contrast to the conventional blood analysis method, significantly smaller amounts of blood are required and, moreover, other equipment, such as syringe bodies and cannulas are eliminated. In addition, taking smaller amounts of blood is significantly simpler, for example, even with regard to maintaining sterile conditions.

In another embodiment according to the invention, a urinal is provided including a urinal pan having at least one ATR body with at least two plane, especially essentially parallel, boundary surfaces, which is transparent to the measuring radiation and has a refractive index which is higher than that of a medium to be investigated, which is adjacent to at least one boundary surface, especially higher than or equal to 1.5, into which a laser beam, especially at least a beam of a quantum cascade laser, preferably at a wavelength in the middle infrared region can be coupled; and/or at least one drain pipe into which a measuring unit, especially a measuring cell containing at least one ATR body with at least two plane boundary surfaces, which is transparent for the measuring radiation and has a refractive index which is higher than that of the medium to be investigated that is adjacent to at least one boundary surface, especially higher than or equal to 1.5 is placed, into which a laser beam, especially at least a beam of a quantum cascade laser, preferably with a wavelength in the middle infrared region, can be coupled. A measuring unit, including the ATR body, can be introduced, for example, in the urinal itself or in the conventional drain pipe of the urinal but, here, preferably, it is introduced in a separate line branched off from the drain pipe. For this embodiment, usually at least two or three, especially at least six or seven attenuated total reflected measuring beams at the boundary wall to the medium are sufficient for a reliable result.

In order to obtain reproducible data, the measuring cell is expediently designed as a flow-through cell with a reversibly closable inlet and outlet. In addition, it was found to be advantageous when the measuring unit or measuring cell can be thermostated, for example, through corresponding channel systems. Furthermore, it is advantageous when a means for cleaning the measuring unit, for example, with cleaning fluid and/or water as well as, optionally, means for drying the measuring unit, for example, a blower, are provided.

Furthermore, an object of another embodiment according to the invention is a toilet, including a toilet bowl, containing at least one ATR body with at least two plane, especially essentially parallel boundary surfaces, which is transparent to the measuring radiation and has a refractive index which is higher than that of a medium to be investigated adjacent to at least one boundary surface, especially higher than or equal to 1.5, into which a laser beam, especially at least one beam of a quantum cascade laser, preferably with a wavelength in the middle infrared region, can be coupled; and/or at least one drain pipe into which a measuring unit, especially a measuring cell containing at least one ATR body with at least two plane, especially essentially parallel boundary surfaces, which is transparent to the measuring radiation and has a refractive index which is higher than that of a medium to be investigated, adjacent to at least one boundary surface, especially greater or equal to 1.5 is placed, into which a laser beam, especially at least a beam of a quantum cascade laser, preferably with a wavelength in the middle infrared region, can be coupled. Usually, for this embodiment, even two or three, especially at least six or seven weakened beams, subjected to attenuated total reflection at the boundary wall to the medium are sufficient for a reliable result. The infrared measuring device or a measuring unit according to the invention can be integrated either into the drain pipe of the toilet or, what is preferable, into a separate line, only one which is branched off from the drain pipe. As in the urinal described above, the measuring cell used in a toilet can also be thermostated. With the feces analysis described above, for example, characteristic data can be obtained for the nature of fats present, as well as regarding their content. In the two embodiments described above, the measuring unit is preferably connected to an inlet for cleaning fluid that can be controlled with a valve with which, after each measuring process, the measuring unit/measuring cell, especially the ATR body, is cleaned.

Furthermore, the present invention includes, in another embodiment, a urinal, including a urinal pan, containing at least one ATR body with at least two plane, especially essentially parallel boundary surfaces, which is transparent to the measuring radiation and which has a refractive index which is higher than that of a medium to be investigated adjacent to at least one boundary wall, especially higher than or equal to 1.5, into which a light beam, especially a beam of an IR light source emitting at least one beam of a continuous spectrum or a multiwavelength spectrum, especially in the infrared region can be coupled; and/or at least one drain pipe into which a measuring unit, especially a measuring cell containing at least one ATR body with at least two plane, especially essentially parallel, boundary surfaces, which is transparent to the measuring radiation and has a refractive index which is higher than that of a medium to be investigated, adjacent to at least one boundary surface, especially higher than or equal to 1.5, into which a light beam, especially at least a beam of an IR light source emitting a continuous spectrum or a multiwavelength spectrum, especially in the middle infrared range, can be coupled. A measuring unit, including the ATR body, can be introduced, for example, in the urinal itself or in the usual drain pipe of the urinal, however, preferably, it is present in a separate line or in a line branched from the drain pipe. For this embodiment, usually even at least two or three, especially at least six or seven measuring beams, subjected to attenuated total reflection at the boundary wall to the medium, are sufficient in order to obtain a reliable result. To obtain reproducible data, the measuring cell is designed expediently as a flow-through cell with a reversibly closable inlet and outlet. In addition, it was found to be advantageous when the measuring unit or measuring cell can be thermostated, for example, through the corresponding channel systems. Furthermore, it is advantageous when means are provided for cleaning the measuring unit, for example, with cleaning fluid and/or water, as well as when means are provided for drying the measuring unit, for example, a blower.

Furthermore, another embodiment according to the invention has a toilet as its object, including a toilet bowl, containing at least one ATR body with at least two plane, especially essentially parallel, boundary surfaces, which is transparent to the measuring radiation and which has a refractive index, which is higher than that of a medium to be investigated, adjacent to at least one boundary surface, especially higher than or equal to 1.5, into which a light beam, especially at least one beam of an IR light source emitting a continuous spectrum or a multiwavelength spectrum, especially in the middle infrared region, can be coupled; and/or at least one drain pipe, into which a measuring unit, especially measuring cell, containing at least one ATR body with at least two plane, especially essentially parallel, boundary surfaces, which is transparent to the measuring radiation and which has a refractive index which is higher than that of a medium to be investigated, adjacent to at least one boundary surface, especially higher than or equal to 1.5 is placed, into which a light beam, especially at least a beam of an IR light source emitting a continuous spectrum or a multiwavelength spectrum, especially in the middle infrared region, can be coupled. The infrared measuring device or a measuring unit according to the invention can be integrated, for example, either into the drain pipe of the toilet or, what is preferred, into a separate line or into a line branched off from the drain pipe. For this embodiment, usually even at least two or three, especially at least six or seven, measuring beams, subjected to attenuated total reflection at the boundary wall to the medium, are sufficient to give a reliable result. As in the case of the urinal described above, the measuring cell used in the toilet can also be thermostated. With the previously described feces analysis, for example, characteristic data can be obtained with regard to the fats present as well as their contents. In the two embodiments described above, the measuring unit is preferably connected to a line for cleaning fluids, which can be controlled with a valve, used to clean the measuring unit/measuring cell, especially the ATR body after each measuring process.

Furthermore, according to the invention, a hollow body, especially a needle, a tube or an immersion probe, with non-transparent side walls, especially with a tapered end, is provided in which, in an end region or at one end, especially at the tapered end of the hollow body, an ATR body is applied tightly, which has at least two plane, essentially parallel boundary surfaces, which is transparent to the measuring radiation and which has a refractive index which is higher than that of a medium to be investigated, adjacent to at least one boundary wall, especially higher than or equal to 1.5, where, through the inside of the hollow body, at least one laser beam, especially that of a quantum cascade laser, can be coupled to the ATR body and at least one IR measuring beam on at least one of plane, parallel boundary surfaces of the ATR body can undergo attenuated total reflection at least six times along a measuring section. In an alternative embodiment of the hollow body, especially needle, tube or immersion probe, an ATR body is applied tightly, additionally or exclusively, on a side wall, that is, for example, on the surface of a needle.

Such hollow bodies are especially suitable as measuring cells or as components, especially of an IR measuring device according to the invention. For example, the said tube or said needle can be used for the invasive determination of components in the blood of living organisms. Based on the small size of the miniature ATR body present in the tip of the needle/tube, with such hollow bodies, real-time measurements can be performed, for example, in a stress test on athletes.

Another embodiment of the invention concerns a cannula, more especially a stent, containing at least one IR measuring cell, especially a flow-through cell, containing at least one ATR body with at least two plane, essentially parallel boundary surfaces, which is transparent to the measuring radiation and has a refractive index, which is higher than the medium to be investigated, adjacent to at least one boundary surface, especially higher than or equal to 1.5, into which a laser beam, especially at least one beam of a quantum cascade laser, preferably with a wavelength in the middle infrared region, can be coupled and at least one IR measuring beam can be subjected to attenuated, total reflection at least six times along the a measuring section, at least on one of the plane, parallel boundary surfaces of the ATR body; and/or at least one previously described hollow body.

Hereby, it is provided that the ATR body of the cannula, which includes especially a previously described infrared measuring device, is in working connection with at least one quantum cascade laser and/or a detector and/or an evaluation unit. Thus, a laser beam can be coupled into the ATR body.

With this cannula, too, quantitative and/or qualitative determination of components can be performed, especially of saccharides, urea, creatinine and/or triglycerides, for example, in the body fluids of living organisms.

Furthermore, according to the invention, a measuring unit/measuring cell is provided containing at least one ATR body for automatic analysis operation, for example, with the aid of an automatic analyzer or robot. This automatic analyzer includes, in addition to the said measuring cell, a rinsing as well as a drying device for the ATR body. In this way, for example, a flow-through cell or a closable flow-through cell or an immersion probe can be cleaned after the measurement process and prepared for the next measurement. The previously described automated method makes very short measuring cycles possible. For example, about 10 seconds are sufficient per measuring process, for example, in order to be able to determine six components, for example, in blood or urine. Thus, using the measuring device according to the invention a number of samples can be measured by infrared spectroscopy in an automated manner.

According to another aspect of the invention, an ATR body is provided, including a first ATR body and a second ATR body, where the first and the second ATR bodies are in contact at least in such a way that the measuring beam can be coupled through the first ATR body into the second ATR body and this measuring beam can be coupled out again from the second into the first ATR body, where the second ATR body has at least two plane, essentially parallel boundary surfaces, of which the first boundary surface can be exposed to a medium to be analyzed and the second boundary surface faces the first ATR body and forms with it at least one closed, especially evacuated or gas-filled cavity. With this embodiment of an ATR body, it is possible to limit the use of expensive, especially insensitive or resistant and/or nontoxic ATR materials, or those which are not soluble in the medium to be analyzed, to that surface area which comes into contact with the medium. Thus, it is possible to use an ATR base body made of zinc selenide, which is generally toxic, or sodium chloride, which dissolves in aqueous media.

The FT-IR measuring device according to the invention as well as the ATR/quantum cascade laser-IR measuring device according to the invention are also especially suitable for the determination of components, especially in food analysis, medicine or veterinary medicine. For example, components can be detected qualitatively and/or quantitatively in body fluids, such as blood, urine, saliva or lymph. In this way, prerequisites for rapid diagnosis are created. Thus, for example, with the aid of a flow-through cell, blood components such as glucose, ureas, creatinine or triglycerides, as well as alcohols, for example, ethanol, can be determined if desired, even on-line, that is, in a real-time mode. Accordingly, the infrared measuring device according to the invention is also suitable for use in dialysis. The replaced blood can be tested continuously for especially relevant or critical components and the time at which the blood is sufficiently purified can be determined exactly. As a result of this, unnecessarily long dialysis times can be avoided. Also, based on the ATR body with small dimensions, it is no problem to use disposable or recyclable flow-through cells in dialysis. Expediently, such a flow-through cell is designed as a module, which can be integrated simply into a measuring section, for example, into a blood-conducting cannula.

Moreover, information about the status of the blood to be purified during dialysis can also be provided by the spectroscopic investigation, carried out with the aid of the infrared measuring device according to the invention, of the washing- or replacement fluid obtained during the purification of the blood. According to the invention, the said measuring device can also be used for the determination of the components in this washing fluid. This also involves the advantage that the measurement no longer has to be performed under sterile conditions, while rapid conclusions about the state of the purified blood can be made possible.

Any current systems used in infrared measuring devices can be employed as detectors for the recording of the measuring beam. In another embodiment, detectors that are known from photoacoustic spectroscopy can also be used. Details on photoacoustic spectroscopy are known to the person skilled in the art and are described, for example, in "Optische Spektroskopie", VCH Verlagsgesellschaft, Weinheim, 1994, Chapter 6.

With the aid of the measuring devices according to the invention, especially the ATR/quantum cascade laser-IR measuring device, it becomes possible to miniaturize the measuring apparatus considerably, without having an adverse effect on the analysis of aqueous multicomponent systems, with regard to measurement accuracy or measurement quality. Here, even the very pronounced water bands in the infrared no longer represent an adverse influence. For example, with the devices according to the invention, wavelength-specific signals can be detected or distinguished which differ in intensity by several times, or even by one or several orders of magnitude, for example, by a factor of 1000. Consequently, with these devices, for example, multicomponent systems can be analyzed which cause strong background noise. In addition, very high light throughput becomes possible with these devices.

For the detection of a substance, measuring radiation even of one given wavelength is always sufficient. Regardless of how many substances are analyzed, it is always sufficient to use only a single reference measuring beam for an exact qualitative and quantitative determination. Thus, for example, when n substances are analyzed with n measuring beams, each of which has a different wavelength, a single reference beam is sufficient for completing the measurement, so that a total of only n+1 beams need to be used.

Finally, with the devices according to the invention, just based on the wavelength-specific intensity information, all data can be obtained which are required for complete analysis without the evaluation of the polarization properties of the measuring beam being necessary.

Other embodiments of the invention are described in detail with the aid of the following drawings, without limiting the invention by these special embodiments. The following are shown:

Figure 1:
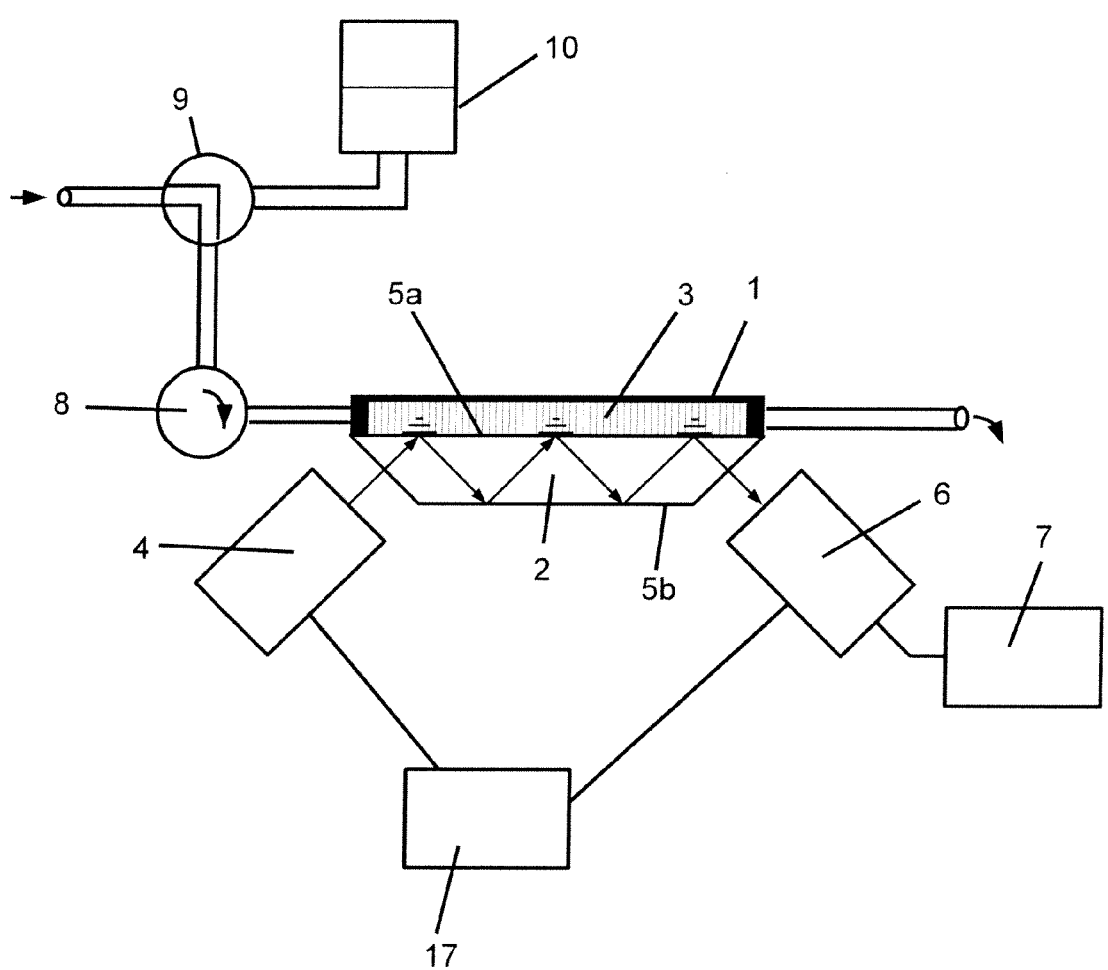
FIG. 1 is an infrared measuring device according to the invention, with flow-through cell in schematic representation.

As can be seen from FIG. 1, an infrared measuring device according to the invention can be equipped with a flow-through cell 1 in an embodiment. A longitudinal wall 5a of the flow-through cell 1 is formed by an ATR body 2 with trapezoidal cross-section. A parallel wall surface 5b delineating the backside of the ATR body lies against the plane boundary surface 5a. The flow-through cell 1 is equipped with a cylindrical channel 3, which mainly passes through the flow-through cell 1 in a straight line. A light beam is introduced through quantum cascade laser 4 through the narrow side of ATR body 2 and impinges on the plane boundary surface 5a, to which the medium to be investigated is adjacent. After several attenuated total reflections, especially at least six or seven such reflections along the measuring section, the exiting light beam is recorded with the aid of a detector 6 and the signal is sent to an evaluation unit 7. A mirror optics is at the radiation source or the detector, not shown, with the aid of which, for example, the beam path can be optimized and controlled. Suitable mirror optics are generally known to the person skilled in the art, especially also in connection with infrared spectrometers. The flow-through of the sample medium is supported with a pump 8, which can be, for example, a peristaltic pump or a piezo pump. Optionally, either the medium to be analyzed or a rinsing- or reference solution, which can also come from a separate container 10, can be passed through the flow-through cell via a control valve 9. In case the solution to be measured should be measured quantitatively, it is recommended to provide a blower (not shown) in order to dry, especially the ATR body, before each new measurement.

In a special embodiment, the flow-through cell 1 can be one which is replaced, that is, by another flow-through cell, for example, also with a different ATR body. Replaceable flow-through cells are used especially when it must be ensured that sterile conditions are maintained and/or that the measured result must not, in any way, be falsified by any residues adhering to the surface of the ATR body remaining from the previously measured sample, for example, in the case of dialysis. The replaced flow-through cell can either be disposed of or recycled.

Furthermore, according to a preferred embodiment, an optical multiplexer 17 can be provided which, first of all, controls the radiation sequence or the radiation pattern, and/or the intensity of the measuring beam of the quantum cascade laser 4 in a wavelength-specific manner and is in working connection with the latter and, on the other hand, which, again in a wavelength-specific manner, controls detector 6 and/or evaluation unit 7, for example, the simultaneous and/or sequential detection of the measuring radiation.

Figure 2:
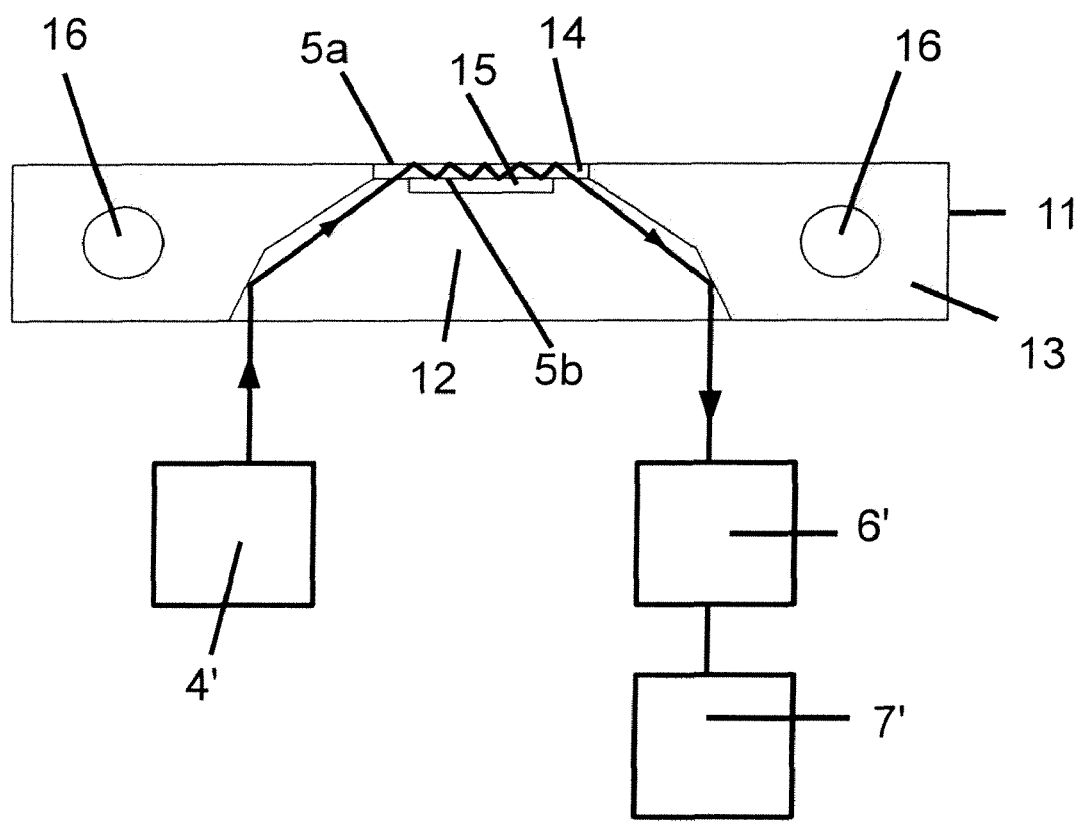
FIG. 2 is a measuring unit according to the invention, in schematic representation in a longitudinal section.

FIG. 2 shows a measuring unit 11 in which a coated, two-part ATR body 12 made essentially of zinc selenite is placed in a holder 13. The ATR basic body 12 made of zinc selenide is provided with a coating or with a separate ATR body, especially in the plate form 14 made of diamond, the one-plane boundary surface 5a of which comes into contact with the medium to be analyzed and the parallel boundary surface to this, 5b, delineates inside the ATR body a cavity 15, which is evacuated or filled with air or gas. The ATR basic body 12 has several plane boundary surfaces at which the incident infrared radiation is reflected. The holder 11 can have a channel or a channel system 16 for thermostating the measuring cell. The infrared beam again exits at light source 4', for example, in the form of a quantum cascade laser, and is recorded with detector unit 6'. The detected signal(s) is(are) analyzed or processed in the evaluation unit 7'. In order to be able to perform accurate infrared spectrometric measurements with the depicted measuring cell, it is sufficient when the side length or the diameter of the boundary surface facing the medium, that is, the measuring section of the diamond layer, lies in the range from about 4 to 5 mm. Sample volumes <100 µL, as well as even those in the range from 5 to 50 µL, that is, for example, 10 µL, can be investigated simply with the measuring cell depicted here with regard to the presence of one or several substances. Several substances can be determined simultaneously next to one another. Naturally, a multiplexer 17, again according to FIG. 1, can be provided (not shown).

The infrared measuring device according to the invention thus permits first of all a simple and reliable and cost-effective access to analysis and characterization, especially of polar substances, for example, those with a hydroxyl function, even in aqueous systems, with high accuracy. Furthermore, another advantage is that, even very small amounts of samples can be detected, especially continuously. It was also found to be advantageous that the infrared measuring device according to the invention, especially the measuring unit used as well as the combination of measuring unit and quantum cascade laser, optionally even including a detector or optical multiplexer, is extremely shock-resistant and, moreover, it permits miniaturized construction.

Figure 3:
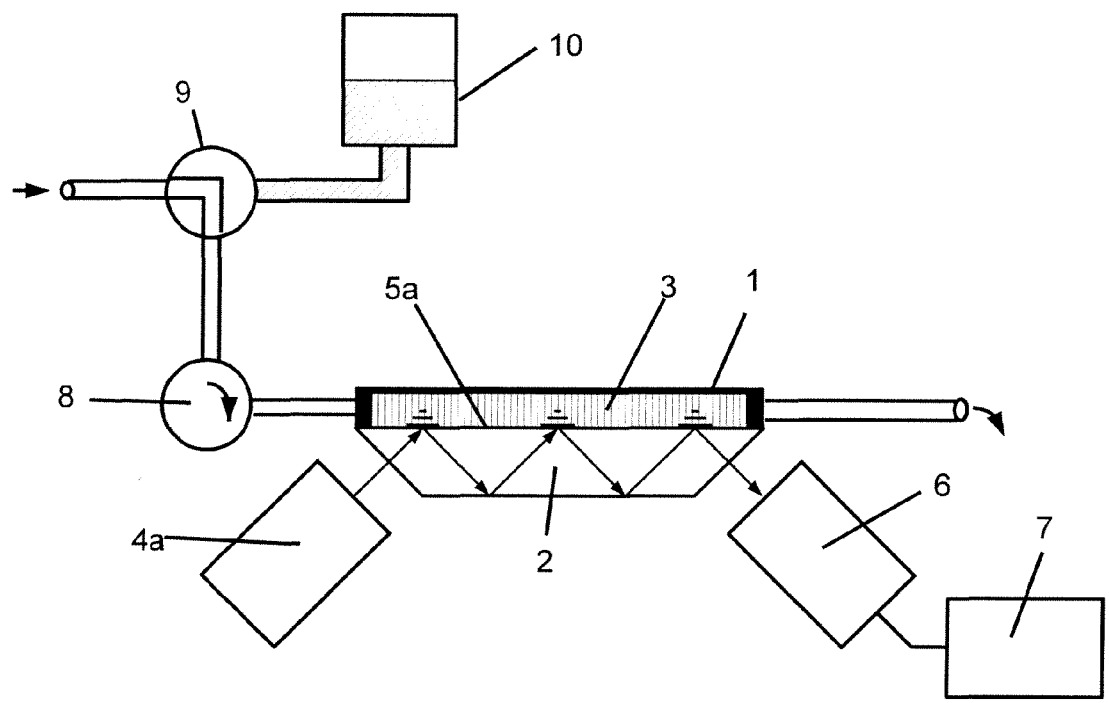
FIG. 3 is an infrared measuring device according to the invention, with flow-through cell in schematic representation.

As can be seen from FIG. 3, the embodiment of an infrared measuring device according to the invention, which uses a measuring radiation with a continuous spectrum, corresponds essentially to the construction shown in FIG. 1. The light beam is introduced through the IR light source 4a, also containing an interferometer, with the aid of which interference-modulated light can be produced, through the narrow side of the ATR body 2 and impinges on the plane boundary surface 5a, to which is adjacent the medium to be investigated is adjacent. After several attenuated total reflections, especially after at least six or seven total reflections, the exiting light beam is recorded with the aid of detector 6 and the signal is further introduced to an evaluation unit 7, with the aid of which the Fourier transformation is performed.

In a special embodiment, the flow-through cell 1 can be one which can be replaced, that is, by another flow-through cell, for example, also one with a different ATR body.

Figure 4:
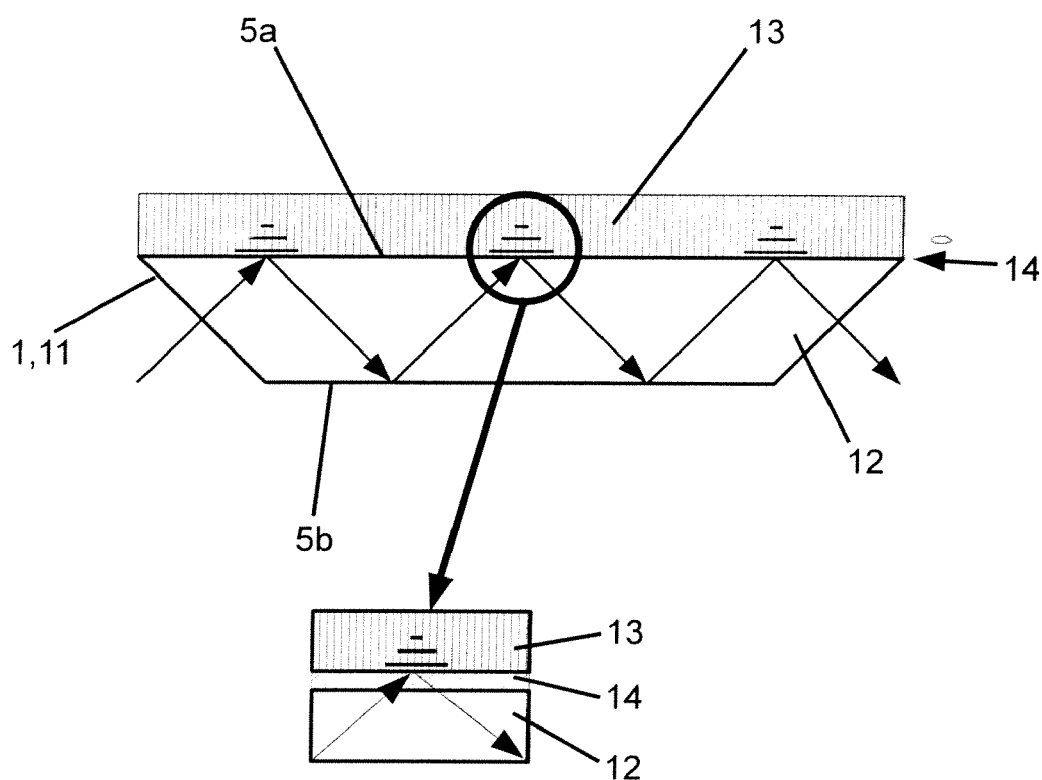
FIG. 4 is a longitudinal section through a coated ATR body.

According to FIG. 4, a measuring unit 1, 11 can include an ATR body 12, especially with trapezoidal cross-section, which is provided with a coating 14, especially a diamond coating on the plane boundary surface 5a, which is exposed to the sample medium. The coating is neighbored by a cavity 13 for holding the sample fluid which can also be designed as a tube or tubular line, with the aid of which the measuring unit 11 can also represent a flow-through cell. Moreover, a section in the region of the coated boundary surface can be seen in FIG. 4 in an enlarged representation.

The characteristics of the invention disclosed in the above Description, in the claims, as well as in the drawings, can be essential both individually as well as in any arbitrary combination, for the realization of the invention in its various embodiments.

REFERENCE LIST

1 measuring cell, flow-through cell
2 ATR body
3 cylindrical channel
4, 4' quantum cascade laser
4a IR light source, containing an interferometer
5a parallel plane boundary surface of ATR body 2
5b plane boundary surface of ATR body 2
6, 6' detector
7, 7' evaluation unit
8 pump
9 control valve 10 separate container for rinsing- and/or reference solution
11 measuring unit
12 coated ATR body
13 holder
14 coating, diamond layer
15 cavity in ATR body 12
16 channel system for the thermostating of measuring unit 11
17 optical multiplexer

The invention claimed is:

1. Infrared (IR) measuring device, for essentially simultaneous, qualitative and quantitative determination of components in nonaqueous and aqueous systems, comprising:
at least one measuring unit having at least one ATR body and at least one infrared light source, wherein the at least one ATR body has at least two plane, essentially parallel boundary surfaces and is transparent or partially transparent to measuring radiation and has a refractive index which is higher than that of the medium to be investigated adjacent to at least one boundary surface where the measuring radiation is middle infrared radiation (MIR) and can undergo attenuated total reflection at least six times on at least one of the plane, parallel boundary surfaces of the at least one ATR body, wherein the at least one infrared light source includes one or more quantum cascade lasers that can emit electromagnetic radiation of at least one defined frequency or of at least one defined frequency band.

2. Infrared measuring device according to claim 1, including at least one computer-aided evaluation unit.

3. Infrared measuring device according to claim 2, wherein the at least one evaluation unit can be replaced by a second or further evaluation units.

4. Infrared measuring device according to claim 1, wherein the plane, essentially parallel boundary surfaces are essentially not metal-coated.

5. Infrared measuring device according to claim 1, wherein the ATR body represents at least one wall of a measuring cell or a part thereof or represents the measuring cell.

6. Infrared measuring device according to claim 1, wherein the ATR body is made of a material selected from the group consisting of diamond, sapphire, cadmium telluride, thallium bromide/iodide, silicon, germanium, zinc selenide, zinc sulfide, magnesium difluoride, cesium iodide, silver chloride, calcium difluoride, potassium bromide, sodium chloride, a material transparent to infrared radiation, a polymeric material with a refractive index of greater than or equal to 1.5 and polyethylene.

7. Infrared measuring device according to claim 1 further including an evaluation unit that implements one or more factorial analyses, multiple least square algorithms or neural network analyses based on the signals entering the detector.

8. Infrared measuring device according to claim 1, wherein at least the ATR body or the measuring unit is thermostated.

9. Infrared measuring device according to claim 1, wherein the ATR body can be placed at least on one boundary surface, which can be exposed to a medium to be analyzed, and includes a coating, which is transparent to the an evanescent field of the measuring radiation.

10. Infrared measuring device according to claim 9, wherein the coating has a thickness which is either smaller than half of the wavelength of the measuring radiation used or in the range from about 2 nm to about 25 μm.

11. The infrared measuring device according to claim 10 wherein the coating has a thickness which is in the range from about 2 μm to about 10 μm.

12. The infrared measuring device according to claim 10, wherein the thickness is both smaller than half of the wavelength of the measuring radiation and in the range from about 2 nm to about 25 μm.

13. Infrared measuring device according to claim 9, wherein the coating has a thickness in the range of one-fourth of the wavelength of the measuring radiation used.

14. Infrared measuring device according to claim 9, wherein the coating has an ATR body material layer and the coated ATR body comprises zinc selenide and/or zinc sulfide.

15. Infrared measuring device according to claim 14, wherein said ATR body material layer is a diamond layer.

16. A method of using the infrared measuring device of claim 1 to perform a chemical analysis, including using the infrared measuring device for the qualitative and/or quantitative determination of one or more components, selected from the group consisting of saccharides, urea, creatinine, triglycerides, carbon dioxide, protein, alcohols, phosphoric acid esters and combinations thereof, in nonaqueous or aqueous systems.

17. The method of claim 16, where one of beer, wine, fruit juice, spirits or soft drinks is used as an aqueous system.

18. The method of claim 16, where one of urine and/or feces is used as an aqueous system.

19. The method of claim 16, where one of lymph, saliva and/or blood is used as an aqueous system.

20. The method of claim 16, where the washing fluid obtained during dialysis is used as an aqueous system.

21. The method of claim 16, where process fluid, waste water or washing liquor is used as an aqueous system.

22. The method of claim 16, wherein the qualitatively and/or quantitatively determination of the presence of one or more components selected from the group consisting of saccharides, urea, creatinine, triglycerides, carbon dioxide, protein, alcohols and/or phosphoric acid esters, in nonaqueous or aqueous systems, is performed essentially simultaneously.

23. A method of using the infrared measuring device according to claim 1, including using the infrared measuring device for the qualitative and/or quantitative determination of components in fruits and vegetables.

24. A method of using the infrared measuring device according to claim 1, including using the infrared measuring device for the qualitative and/or quantitative determination of components in milk and dairy products.

25. The infrared measuring device of claim 1, wherein the refractive index is higher than or equal to 1.5.

26. The infrared measuring device of claim 1, wherein the one or more quantum cascade lasers can emit electromagnetic radiation of at least two defined frequencies.

27. The infrared measuring device of claim 1, wherein the one or more of the quantum cascade lasers can emit the electromagnetic radiation of the at least one defined frequency or the defined frequency band at a predetermined and defined intensity.

28. A method comprising using the measuring device of claim 1 for the quantitative and/or qualitative determination of two, three, four, five, six or more components in multicomponent mixtures in the body fluids of living organisms.

29. Infrared (IR) measuring device, for essentially simultaneous, qualitative and quantitative determination of components in nonaqueous and aqueous systems, comprising:
at least one measuring unit having at least one ATR body and at least one infrared light source, wherein the at least one ATR body has at least two plane, essentially parallel boundary surfaces and is transparent or partially transparent to measuring radiation and has a refractive index which is higher than that of the medium to be investigated adjacent to at least one boundary surface where the measuring radiation is middle infrared radiation (MIR) and can undergo attenuated total reflection at least six times on at least one of the plane, parallel boundary surfaces of the at least one ATR body, wherein the infrared light source includes one or several quantum cascade lasers wherein two or more of the quantum cascade lasers can emit electromagnetic radiation of different frequencies and/or of different frequency bands, in the middle infrared region.

30. Infrared measuring device according to claim 29, wherein the two or more quantum cascade lasers can simultaneously or almost simultaneously emit the electromagnetic radiation of the different frequencies, and/or of the different frequency bands.

31. The infrared measuring device of claim 29, wherein the two or more of the quantum cascade lasers can emit the electromagnetic radiation of the different frequencies or of the different frequency bands at predetermined and defined intensities.

32. Infrared (IR) measuring device, for essentially simultaneous, qualitative and quantitative determination of components in nonaqueous and aqueous systems, comprising:
    at least one measuring unit having at least one ATR body and at least one infrared light source, wherein the at least one ATR body has at least two plane, essentially parallel boundary surfaces and is transparent or partially transparent to measuring radiation and has a refractive index which is higher than that of the medium to be investigated adjacent to at least one boundary surface where the measuring radiation is middle infrared radiation (MIR) and can undergo attenuated total reflection at least six times on at least one of the plane, parallel boundary surfaces of the at least one ATR body, including one or more quantum cascade lasers that can emit electromagnetic radiation of different frequencies, and/or of different frequency bands in a time sequence.

33. The infrared measuring device of claim 32, wherein the one or more of the quantum cascade lasers can emit the electromagnetic radiation of the different frequencies or of the different frequency bands at predetermined and defined intensities.

34. Infrared (IR) measuring device, for essentially simultaneous, qualitative and quantitative determination of components in nonaqueous and aqueous systems, comprising:
    at least one measuring unit having at least one ATR body and at least one infrared light source, wherein the at least one ATR body has at least two plane, essentially parallel boundary surfaces and is transparent or partially transparent to measuring radiation and has a refractive index which is higher than that of the medium to be investigated adjacent to at least one boundary surface where the measuring radiation is middle infrared radiation (MIR) and can undergo attenuated total reflection at least six times on at least one of the plane, parallel boundary surfaces of the at least one ATR body, including at least one quantum cascade laser that can emit electromagnetic radiation in the form of pulses with defined duration.

35. Infrared measuring device according to claim 34, wherein the duration of the pulses differs in length and/or the intensity of the pulses differs in magnitude.

36. Infrared measuring device according to claim 34, wherein different frequencies or frequency bands of electromagnetic radiation originating from the at least one quantum cascade laser can be emitted sequentially or in any arbitrary sequence.

37. Infrared measuring device according to claim 36, wherein the measuring radiation and/or its intensity can be detected according to a multiplex pattern in a wavelength-specifically controllable, pulsewise emittable manner, and/or according to a multiplex pattern of the measuring radiation in a pulsed form.

38. The infrared measuring device of claim 34, wherein the at least one quantum cascade laser can emit the electromagnetic radiation in the form of the pulses each with a predetermined and defined intensity.

39. Infrared (IR) measuring device, for essentially simultaneous, qualitative and quantitative determination of components in nonaqueous and aqueous systems, comprising:
    at least one measuring unit having at least one ATR body and at least one infrared light source, wherein the at least one ATR body has at least two plane, essentially parallel boundary surfaces and is transparent or partially transparent to measuring radiation and has a refractive index which is higher than that of the medium to be investigated adjacent to at least one boundary surface where the measuring radiation is middle infrared radiation (MIR) and can undergo attenuated total reflection at least six times on at least one of the plane, parallel boundary surfaces of the at least one ATR body,
    wherein the at least one infrared light source comprises
    a quantum cascade laser able to emit electromagnetic radiation in at least two different defined frequencies or one or more frequency bands,
    a plurality of quantum cascade lasers each being able to emit electromagnetic radiation at one or more frequencies or frequency bands, or
    a radiation source emitting a multi-wavelength spectrum.

40. Urinal, or a urinal pan, comprising:
    at least one ATR body, with at least two plane, essentially parallel boundary surfaces, which is transparent to middle infrared radiation (MIR), and has a refractive index which is higher than that of a medium to be investigated, which is adjacent to at least one boundary surface, into which a laser beam and/or at least one discharge line, into which a measuring unit containing the at least one ATR body with at least two plane, essentially parallel boundary surfaces, which is transparent or partially transparent to a measuring radiation, and has a refractive index, which is higher than that of the medium to be investigated adjacent to at least one boundary surface, into which a laser beam can be coupled, wherein the laser beam is a beam of a quantum cascade laser.

41. Toilet, including a toilet bowl, comprising:
    at least one ATR body with at least two plane, essentially parallel boundary surfaces, which is transparent to middle infrared radiation (MIR), and which has a refractive index, which is higher than that of a medium to be investigated, which is adjacent to at least one boundary surface into which a laser beam can be coupled; and/or at least a drain pipe, into which a measuring unit containing the at least one ATR body with at least two plane, essentially parallel boundary surfaces, which is transparent or partially transparent to a measuring radiation and has a refractive index which is higher than that of a medium to be investigated, which is adjacent to at least one boundary surface is placed, into which a laser beam can be coupled, wherein the laser beam is a beam of a quantum cascade laser.

42. Cannula comprising:
    at least one measuring cell containing at least one ATR body with at least two plane, essentially parallel, boundary surfaces which is transparent or partially transparent to middle infrared radiation (MIR), and which has a refractive index which is higher than that of the medium being investigated, which is adjacent to at least one of the boundary surfaces, into which at least one beam of a quantum cascade laser can be coupled and at least one infrared measuring beam can undergo attenuated total reflection at least six times along the measuring section, on at least one of the plane, parallel boundary surfaces of the ATR body; and at least one hollow body.

43. Cannula according to claim 42, comprising
an infrared measuring device having the at least one ATR body and at least one infrared light source, wherein the measuring unit contains the at least one ATR body, which has at least two plane, essentially parallel boundary surfaces, which are transparent or partially transparent to the measuring beam and which have a refractive index which is higher than that of the medium to be investigated adjacent to at least one boundary surface, where the measuring beam contains middle infrared radiation (MIR) and can undergo attenuated total reflection at least six times on at least one of the plane, parallel boundary surfaces of the at least one ATR body, wherein the at least one ATR body is in working connection with at least one quantum cascade laser and/or a detector and/or an evaluation unit.

44. A method comprising using the cannula of claim 42 for the quantitative and/or qualitative determination of two, three, four, five, six or more components in multicomponent mixtures.

45. The method according to claim 44, wherein said components are selected from the group consisting of saccharides, urea, creatinine, and triglycerides.

46. The cannula of claim 41, wherein the refractive index is higher than or equal to 1.5.

47. Cannula according to claim 42, wherein the cannula is a stent.

* * * * *

UNITED STATES PATENT AND TRADEMARK OFFICE
CERTIFICATE OF CORRECTION

PATENT NO. : 7,812,312 B2  
APPLICATION NO. : 10/510017  
DATED : October 12, 2010  
INVENTOR(S) : Werner Mäntele et al.

Page 1 of 1

It is certified that error appears in the above-identified patent and that said Letters Patent is hereby corrected as shown below:

On the Title Page:

Item (75), "Christian Zscherp, Freiberg-Ossenheim" should be -- Christian Zscherp, Friedberg-Ossenheim --.

Item (75), "Hermann Von Lillienfeld-Toal" should be -- Hermann Von Lilienfeld-Toal --.

Signed and Sealed this
Ninth Day of August, 2011

David J. Kappos
*Director of the United States Patent and Trademark Office*